US010842931B2

(12) United States Patent
DeArmond et al.

(10) Patent No.: US 10,842,931 B2
(45) Date of Patent: Nov. 24, 2020

(54) SYSTEM OF INTRAVENOUS FLUID/MEDICATION DELIVERY THAT EMPLOYS SIGNATURE FLOW AMPLITUDES OF FREQUENCIES TO FACILITATE THE DETECTION OF INTRAVENOUS INFILTRATION

(71) Applicant: The Board of Regents of the University of Texas System, Austin, TX (US)

(72) Inventors: Daniel T. DeArmond, San Antonio, TX (US); John H. Calhoon, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 177 days.

(21) Appl. No.: 14/652,888

(22) PCT Filed: Dec. 12, 2013

(86) PCT No.: PCT/US2013/074643
§ 371 (c)(1),
(2) Date: Jun. 17, 2015

(87) PCT Pub. No.: WO2014/099602
PCT Pub. Date: Jun. 26, 2014

(65) Prior Publication Data
US 2015/0335820 A1    Nov. 26, 2015

Related U.S. Application Data

(60) Provisional application No. 61/738,042, filed on Dec. 17, 2012.

(51) Int. Cl.
*A61M 5/168*    (2006.01)

(52) U.S. Cl.
CPC .... *A61M 5/16831* (2013.01); *A61M 5/16836* (2013.01); *A61M 2005/16863* (2013.01);
(Continued)

(58) Field of Classification Search
CPC ............ A61M 5/1681; A61M 5/16836; A61M 2205/3375; A61M 2250/00; A61M 2230/30; A61M 2005/16863
See application file for complete search history.

(56) References Cited

U.S. PATENT DOCUMENTS 4,406,878 A    9/1983 Deboer
4,411,652 A    10/1983 Kramer et al.
(Continued)

FOREIGN PATENT DOCUMENTS

EP    0248632    12/1987
WO    01/97905    12/2001

OTHER PUBLICATIONS

Bruce et al. "Systematic review of the definition and measurement of anastomotic leak after gastrointestinal surgery," British Journal of Surgery, 2001, vol. 88, pp. 1157-1168.
(Continued)

*Primary Examiner* — William R Carpenter
*Assistant Examiner* — Hamza A Darb
(74) *Attorney, Agent, or Firm* — Kowert, Hood, Munyon, Rankin & Goetzel, P.C.; Mark R. DeLuca

(57) ABSTRACT

Occlusion of a vein during IV fluid treatment, in some embodiments, may be detecting by delivering predetermined flow patterns (e.g., flow frequencies and/or amplitudes) of fluid to the subject and monitoring the flow of the fluid downstream vein. A deviation of the flow pattern downstream from the vein from the predetermined flow pattern may be used to determine if an occlusion has occurred. A system for monitoring fluid delivery to a subject includes, in
(Continued)

some embodiments, a pump system capable of delivering flow with predetermined flow rates and one or more flow detectors capable of detecting downstream peripheral venous flow.

10 Claims, 15 Drawing Sheets

(52) U.S. Cl.
CPC . *A61M 2205/3375* (2013.01); *A61M 2230/30* (2013.01); *A61M 2250/00* (2013.01)

(56) References Cited

U.S. PATENT DOCUMENTS

| | | | |
|---|---|---|---|
| 4,697,593 A | 10/1987 | Evans et al. | |
| 5,357,956 A | 10/1994 | Nardella | |
| 5,749,369 A | 5/1998 | Rabinovich et al. | |
| 5,828,184 A | 10/1998 | Nadd | |
| 5,916,171 A | 6/1999 | Mayevsky | |
| 6,090,048 A | 7/2000 | Hertz et al. | |
| 6,167,765 B1* | 1/2001 | Weitzel | A61M 1/3663 600/454 |
| 6,193,669 B1* | 2/2001 | Degany | A61B 5/02014 600/486 |
| 6,360,123 B1 | 3/2002 | Kimchi et al. | |
| 6,405,079 B1 | 6/2002 | Ansarinia | |
| 6,425,877 B1 | 7/2002 | Edwards | |
| 6,512,949 B1 | 1/2003 | Combs et al. | |
| 6,526,318 B1 | 2/2003 | Ansarinia | |
| 7,245,954 B2 | 7/2007 | Glukhovsky | |
| 8,197,235 B2 | 6/2012 | Davis | |
| 8,286,505 B2 | 10/2012 | Wade | |
| 8,348,850 B2 | 1/2013 | Frinak et al. | |
| 8,486,019 B2 | 7/2013 | White et al. | |
| 8,568,349 B2 | 10/2013 | Shergold | |
| 8,636,670 B2 | 1/2014 | Ferren et al. | |
| 8,668,672 B2 | 3/2014 | Moberg et al. | |
| 8,672,876 B2 | 3/2014 | Jacobson et al. | |
| 8,679,075 B2 | 3/2014 | Lurvey et al. | |
| 8,696,632 B2 | 4/2014 | Gillespie, Jr. et al. | |
| 8,702,656 B2 | 4/2014 | Kamen et al. | |
| 8,739,601 B2 | 6/2014 | Stringham et al. | |
| 2003/0216663 A1 | 11/2003 | Jersey-Willuhn et al. | |
| 2004/0133079 A1 | 7/2004 | Mazar et al. | |
| 2004/0254432 A1 | 12/2004 | Necola Shehada et al. | |
| 2005/0124908 A1 | 6/2005 | Belalcazar | |
| 2008/0132797 A1* | 6/2008 | Brabrand | A61M 5/16831 600/504 |
| 2011/0137241 A1 | 6/2011 | Delcastilio et al. | |
| 2011/0152697 A1 | 6/2011 | Kawamura | |
| 2012/0312073 A1 | 12/2012 | Stringham et al. | |
| 2012/0323127 A1 | 12/2012 | Boyden et al. | |
| 2013/0123743 A1 | 5/2013 | Adams | |
| 2013/0138041 A1 | 5/2013 | Smisson, III et al. | |
| 2013/0310770 A1 | 11/2013 | Cooke et al. | |
| 2013/0317373 A1 | 11/2013 | Warren et al. | |
| 2013/0331707 A1 | 12/2013 | Alley et al. | |
| 2013/0345658 A1 | 12/2013 | Browne et al. | |
| 2014/0107613 A1 | 4/2014 | Keith et al. | |
| 2014/0171770 A1 | 6/2014 | Hann | |

OTHER PUBLICATIONS

Heiken et al., "CT Evaluation after Esophagogastrectomy," American Journal of Roentgenology (AJR), 1984, vol. 143, pp. 555-560. (Abstract).

Herrlin, K., "The Diagnosis of Anastomotic Leak After Gastroesophagostomy with Biliary Scintigraphy," Clinical Nuclear Medicine, 1995, vol. 20, pp. 709-711. (Abstract).

Junger et al., "Early detection of anastomotic leaks after colorectal surgery by measuring endotoxin in the drainage fluid," Hepatogastroenterology, 1996, abstract as displayed from PubMed; 1 page. (Abstract).

Marshall et al, "Roux-en-Y Gastric Bypass Leak Complications," Archives of Surgery, 2003, vol. 138, pp. 520-524. (American Meidacl Association). (Abstract).

Ovnat et al., "Early Detection and Treatment of a Leaking Gastrojejunostomy Following Gastric Bypass," Israel Journal of Mecial Sciences, 1986, vol. 22, pp. 556-558 (Abstract).

Sing et al, "Sensitivity and specificity of postoperative upper GI series following gastric bypass," Obesity Surgery, 2003, abstract as displayed from PubMed; 1 page (Abstract).

International Search Report / Written Opinion for PCT Application No. PCT/US2013/074643 dated Mar. 31, 2014.

International Preliminary Report on Patentability for PCT Application No. PCT/US2013/074643 dated Jun. 23, 2015.

* cited by examiner

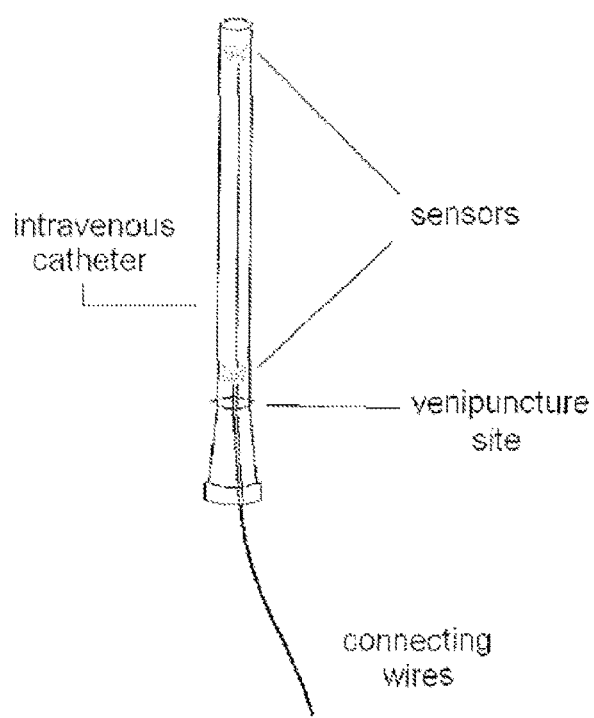
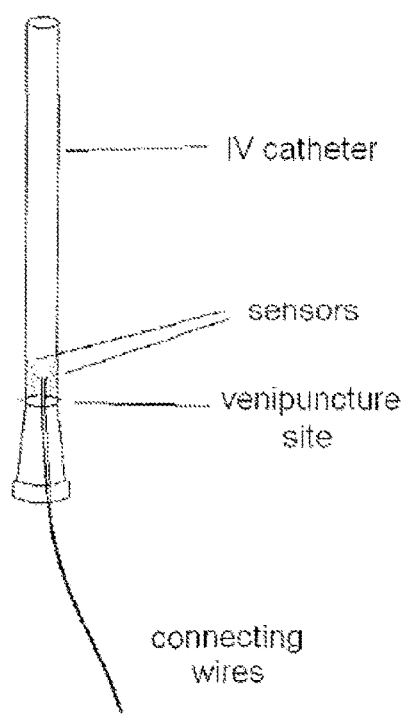
FIG. 3A
FIG. 3B

SYSTEM OF INTRAVENOUS FLUID/MEDICATION DELIVERY THAT EMPLOYS SIGNATURE FLOW AMPLITUDES OF FREQUENCIES TO FACILITATE THE DETECTION OF INTRAVENOUS INFILTRATION

BACKGROUND OF THE INVENTION

1. Field of the Invention

The invention generally relates to the intravenous delivery of fluids. More particularly the invention relates to systems and methods of monitoring intravenous catheter/cannula-associated venous occlusion.

2. Description of the Relevant Art

An estimated 150 million intravenous ("IV") devices are placed in hospitals in the United States each year for the delivery of fluids and/or medications. The most common complication of these devices is IV infiltration, also referred to as phlebitis, that may result in substantial patient morbidity and that, at a minimum, requires removal and replacement of the IV. The risk of IV infiltration has been quoted as ranging from 2-67% of all IV lines. In one recent large study, roughly one third of all IV lines had to be replaced due to phlebitis. This has led hospitals to adapt labor-intensive algorithms that involve the regular rotation of IV lines every 2-3 days. Unfortunately, these practices have not clearly been demonstrated to reduce the rates of phlebitis.

Phlebitis leads to venous occlusion, usually the result of a blood clot forming in the vein. When a clot forms in a vein into which (IV) drugs and other fluids are being infused, fluid flow in the vein ceases and fluid flow is diverted to the extra-vascular subcutaneous tissues, (a condition referred to as tissue extravasation or tissue infiltration), causing tissue swelling and tissue damage. Occlusion-related tissue extravasation of drugs and fluids is especially a problem in the elderly owing to the fragile veins in the elderly due to a paucity of supporting tissues. Tissue damage is especially likely when anti-cancer chemotherapy drugs leak into extravascular tissues.

There is, therefore, a need for improved, less labor-intensive phlebitis surveillance.

SUMMARY OF THE INVENTION

In an embodiment, a system for monitoring venous fluid flow in a subject includes: a pump system that, during use, delivers a liquid to a vein of the subject in a predetermined flow pattern; and a flow probe coupled to the pump system, the flow probe being capable of detecting the flow rate of the liquid through a vein.

In an embodiment, the pump system comprises a pump and an inline impulse generating apparatus, wherein the liquid is sent from the pump to the inline impulse generating apparatus, and wherein the inline impulse generating apparatus creates the predetermined flow pattern in the liquid. In an embodiment, a tube containing the liquid passes through the inline impulse generating apparatus. The inline impulse generating apparatus creates a fluid pulse by altering the diameter of the tube containing the liquid within the inline impulse generating apparatus. In an embodiment, the inline impulse generating apparatus includes a tube through which the liquid is conveyed, a magnetic coil positioned proximate to the tube, and a permanent magnet positioned proximate to the tube and opposite to the magnetic coil. During use, the polarity of the magnetic field generated by the magnetic coil can be altered, causing the permanent magnet to move toward or away from the magnetic coil. In this way, a flow pattern may be generated in the liquid flowing through the tubing.

The pump system, in some embodiments, includes a controller coupled to the inline impulse generating apparatus, and the flow probes. The controller is programmable to control the flow pattern produced by the inline impulse generating apparatus. The controller also may provide a signal when the flow pattern detected by the flow probe is different from the predetermined flow pattern.

In an embodiment, the flow probe may be a Doppler flow probe. In another embodiment, one or more electrolyte probes are coupled to the pump system capable of detecting extra-vascular or intra-vascular electrolyte changes. A catheter may be coupled to the pump system, wherein one or more electrolyte probes are coupled to an exterior or interior surface of the catheter.

In an embodiment, a method of providing intravenous fluids to a subject includes: coupling an intravenous fluid source to the pump system of a system for monitoring venous fluid flow as described above; sending the intravenous fluid to the subject through a catheter in a predetermined flow pattern; monitoring the flow pattern of the fluid using a flow probe; and providing a signal when the flow pattern detected by the flow probe is different from the predetermined flow pattern. The intravenous fluid may be blood, plasma, or saline. The intravenous fluid may include a medicine. The flow probe may be positioned downstream from the catheter or upstream from the catheter. In some embodiments, the flow probe may is positioned to monitor fluid flow through the catheter.

BRIEF DESCRIPTION OF THE DRAWINGS

Advantages of the present invention will become apparent to those skilled in the art with the benefit of the following detailed description of embodiments and upon reference to the accompanying drawings in which:

FIGS. 3A-3B depict IV catheters that house sensors to detect electrical or other changes in the intravascular tissues;

Figure 1:
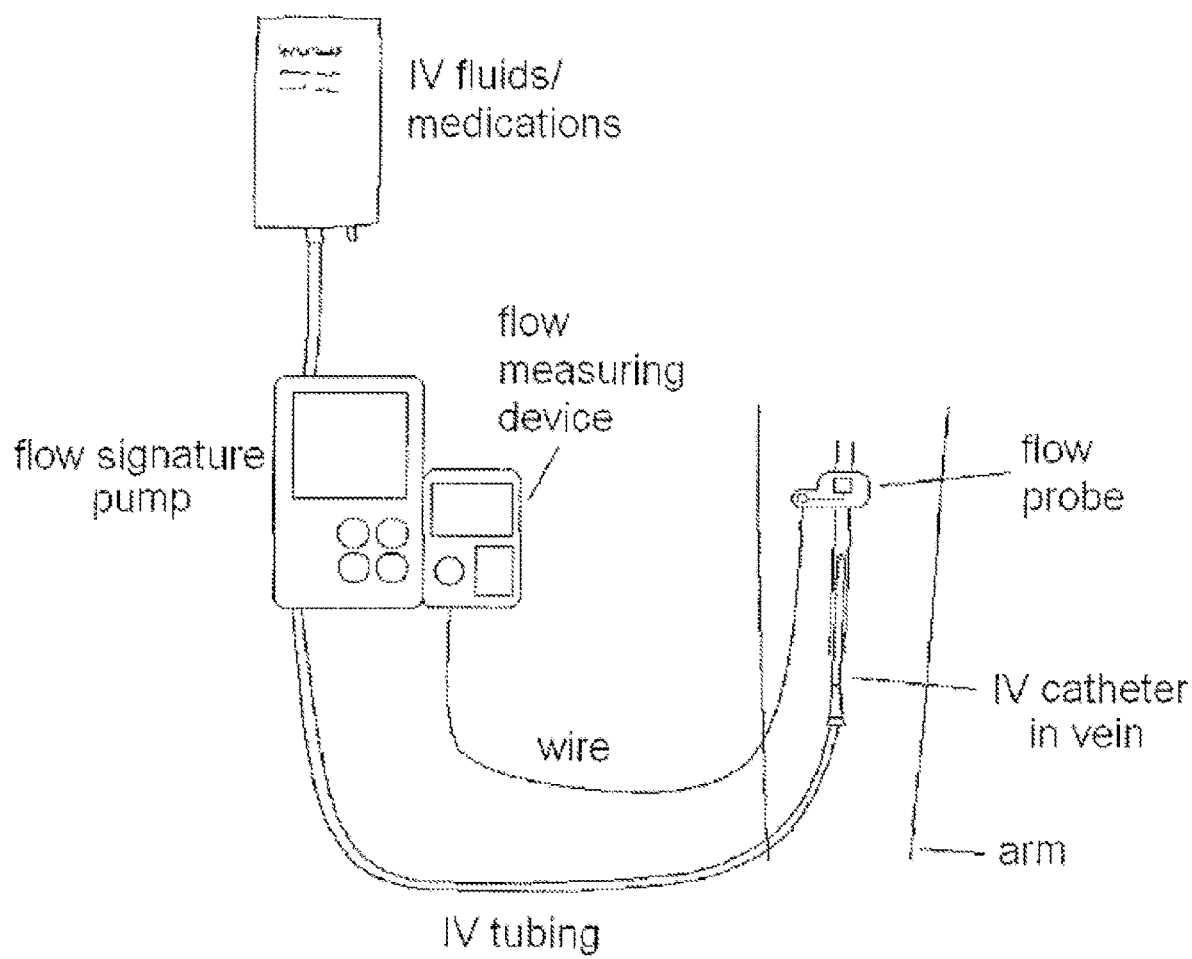
FIG. 1 depicts a schematic diagram of an embodiment of a system used to monitor the flow of IV fluids through the vein of a subject.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

As discussed above, when phlebitis occurs the vein becomes occluded. As a result, fluid flow in the vein ceases and fluid flow is diverted to the extra-vascular subcutaneous tissues, causing tissue swelling and damage. Approaches to identifying IV infiltration early would be to identify the interruption of the flow of IV fluids in the vein downstream of the IV device and/or to identify electrical changes in the extra-vascular subcutaneous tissues due to tissue swelling. Conventional IV delivery systems deliver a slow, uniform flow of IV fluids at a set rate which is difficult to monitor and the interruption of such flow may produce a non-specific signal change. If IV fluids were delivered using signature flow frequencies and/or amplitudes, preserved flow in the downstream vein would be more readily identifiable as would its interruption. Furthermore, measurement of electrical changes in the tissues might be able to identify the transfer of the signature flow frequency and/or amplitude from the intravascular to the extra-vascular space.

In an embodiment, a system for monitoring the flow of IV fluids through the veins of a subject include: an IV pump capable of delivering fluid flow with specific, signature flow frequencies and/or amplitudes; a flow probe capable of detecting flow of the fluid through a tube or blood vessel; a sensor to detect electrical changes in the extravascular subcutaneous tissues; and a controller coupled to the flow detector that is capable of identifying the specific, signature flow frequencies and/or amplitudes in the intravascular versus extra-vascular compartments.

FIG. 1 depicts a schematic diagram of an embodiment of a system used to monitor the flow of IV fluids through the vein of a subject. A flow signature pump delivers IV fluids/medications with a signature flow or pressure pattern (see description of signature pattern discussed below). A flow probe is placed over the downstream vein and detects changes in flow as a signal. While the flow probe is depicted as monitoring the flow through the downstream vein, in alternate embodiments, the flow probe may monitor fluid flow through the IV tubing or through the catheter. The flow probe feeds the received signal back to a flow measuring device that tries to match that signal with the signal being delivered by the pump. If the signals match, the measuring device concludes that the vein is patent; if the signal is absent or differs from what the pump is delivering, the measuring device concludes that the IV has infiltrated and/or is non-functioning and the device produces a signal (e.g. an alarm) indicating possible occlusion of the vein.

Signature patterns of flow or pressure would include any pattern of fluid flow that could be differentiated from background movement or noise from the body part where the IV line was located. Simple pulsatile flow is not as useful as a signature pattern because there are pulses in the body and any regular movement of, for example, the arm where the IV was placed could be mistaken for the signal or an alteration in the signal. Also, simple, regular sine or square waves of fluid flow might not qualify as a distinctive signature pattern because too many background movements could mimic the signal. In other embodiments, the signature pattern may be a predetermined pattern of: conducted electrical signals; magnetic polarization signals; laser or light signals; chemical signals; or temperature signals.

Figure 2:
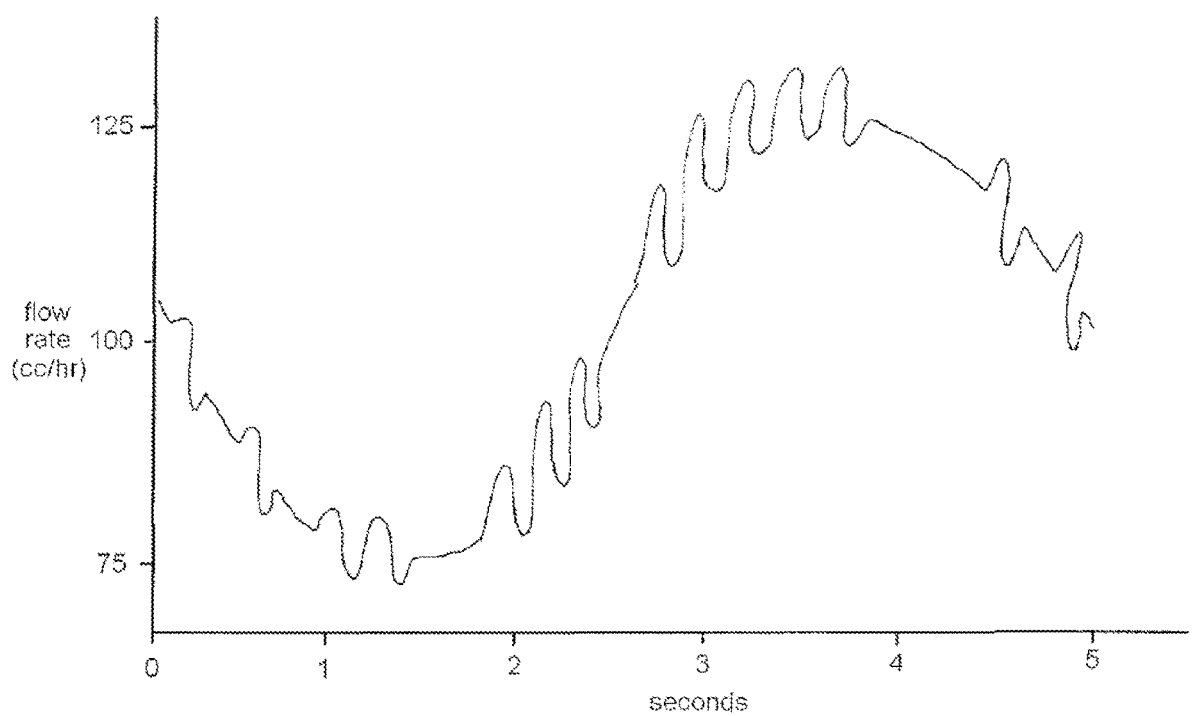
FIG. 2 depicts a sine wave pattern of flow with an overlay of intermittent pulses.

Signature flow or pressure patterns would, in one embodiment, include a sine, square or saw-tooth pattern of flow with an overlay of intermittent pulses determined by, for example, a mathematical series. In FIG. 2, a sine wave flow rate with a wavelength of 5 seconds and amplitude ranging between 125 cc/hr and 75 cc/hr contains an overlay of impulses dictated by a defined sequence of numbers (0, 1, 1, 2, 3, 5).

The signature wave pattern shown in FIG. 2 would, on average, deliver an IV fluid rate of 100 cc/hr. Any combination of waves and sequence of impulses would be possible with different signature flow patterns employed in different situations. Importantly, by alternating the flow this way instead of delivering a slow, regular flow as conventional IV pumps do, it may be possible to decrease the incidence of phlebitis similarly to the mechanisms sequential compression devices use to decrease the risk of deep vein thrombosis.

Flow detection is possible using a number of Doppler technologies and is widely employed in clinical practice either with rudimentary hand-held Doppler devices at the bedside or in the clinic or Doppler imaging in vascular and echocardiogram laboratories. However, a low signal-to-noise ratio makes it difficult to reliably distinguish the slow, bland fluid flow through smaller vascular structures such as peripheral veins from the surrounding tissues. By providing a signature to the pattern of flow, this invention provides a signal by which a detector can identify the presence or absence of flow in smaller structures to improve the signal-to-noise ratio.

Other devices, other than Doppler based devices, maybe used to assess fluid velocimetry within the vein or IV catheter. Other technologies that may be employed include, but are not limited to: particle image velocimetry, particle tracking velocimetry, molecular tagging velocimetry, laser-based interferometry, light absorbance or transmittance, and chemical or temperature signal identification.

In some embodiments, the IV catheter itself could also be configured to house sensors to detect electrical or other changes in the intra- or extra-vascular tissues. When an IV infiltrates, flow that was previously intravascular is diverted into extravascular tissue compartments, resulting in a change in the electrical properties of those compartments. The same signature flow pattern detected by the flow probe may also be detected by sensors detecting electrical changes in the extra-vascular compartments in the presence of IV infiltration with diversion of flow. An IV catheter could be configured to have sensors on the outside of the catheter in contact with or influenced by the extra-vascular tissues to detect electrical changes. Alternatively, the electrodes may be housed on the intra-luminal side of the angiocatheter. Two possible configurations are presented in FIGS. 3A and 3B. Systems and methods of measuring changes in electrolytes leaked into a body cavity are described in U.S. Pat. No. 7,899,508 issued on Mar. 1, 2011, which is incorporated herein by reference.

Signature flow could also be applied to other medical pumps where the goal would be to decrease the likelihood of occlusion or thrombus formation and/or be able to identify occlusion early, for example, in pumps used for delivering nutritional fluids via enteral feeding tubes, in cardiopulmonary bypass circuits or central venous catheters, or for insulin or other drug delivery, etc. Signature flow could also be employed in arteries, for example during coronary angiography or extremity angiography, with an angiography catheter delivering the signature flow pattern into the artery; a dampened or absent signature flow as detected distally in the artery by a flow meter or by electrodes embedded on the outside or inside of the angiocatheter could signal the presence of critical stenosis of the artery in question.

In one embodiment, the impulse-delivering capability and the impulse-detecting capability may be incorporated into a conventional intravenous pump. This embodiment would have the advantage of allowing the intravenous pump itself to be capable of detecting IV infiltration and keep all of the functionality in one package. The translating actuators of typical, linear peristaltic IV pumps may be configured to deliver the impulse signatures in addition to their function of creating forward fluid flow. A controller unit within the pump may translate signals from the fluid probe into a waveform that could be displayed: on a screen on the pump itself; transmitted to a separate continuous monitoring video screen; or into a tracing on paper.

In another embodiment, a device may be mounted onto the IV tubing between the IV pump and the patient, which includes the ability to deliver the impulse pattern by acting on the IV tubing and the ability to translate signals from the flow probe into a waveform that could be displayed: on a screen on the device itself; transmitted to a separate continuous monitoring video screen; or into a tracing on paper.

In another embodiment, no IV pump would be involved in the system at all. Instead, a free-standing IV catheter in a patient could be directly connected to a device that contained the impulse-generating functionality but no IV pump. Such a device also includes the ability to translate signals from the probe sensor into a waveform that could be displayed: on a screen on the device itself; transmitted to a separate continuous monitoring video screen; or into a tracing on paper. The advantage of this embodiment would be that immediately after IV catheter placement, for example in the operating room in an anesthetized patient, the IV could be interrogated before attaching it to an IV pump to make sure the IV catheter was in the lumen of the vein and not inadvertently placed into the subcutaneous tissues outside the lumen of a vein.

In other embodiments of the impulse detection system, a computer central processing unit would be designed to perform signal analysis of the signal detected by the flow probe to determine whether or not the delivered impulse pattern was present. Alteration or loss of the signal of impulses delivered, as identified by the computer, would trigger the computer to issue an alarm alerting caregivers of the need to interrupt and/or analyze the IV catheter to make sure occlusion/infiltration was not present.

Figure 4:
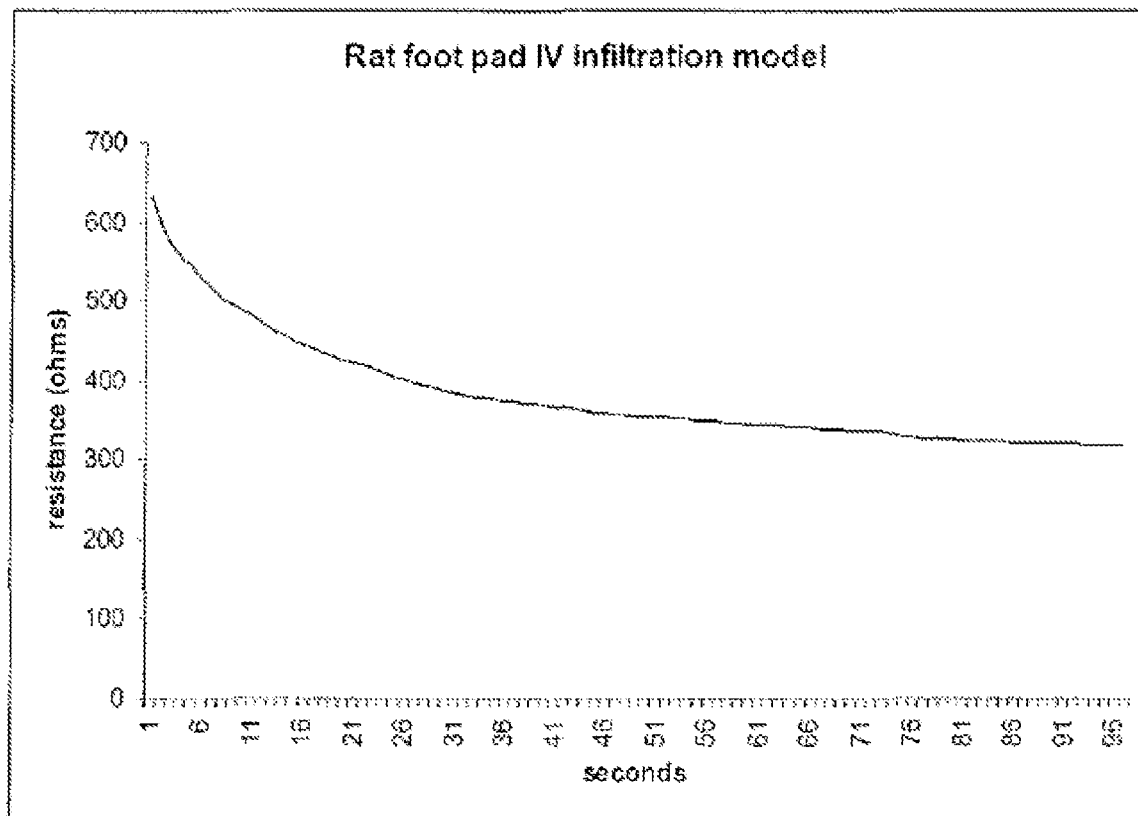
FIG. 4 depicts the change in bioimpedance associated with the extravasation of electrolyte fluid into the extra-vascular tissue compartments.

In one experiment, a rat foot-pad model of IV infiltration was performed to demonstrate that bioimpedance can readily detect the changes associated with the extravasation of electrolyte fluid into the extra-vascular tissue compartments of the extremity. FIG. 4 shows the results of this experiment. As IV fluids were introduced with a uniform flow rate into the foot-pad the resistance of the tissues steadily dropped as detected by bioimpedance electrodes; signature flow patterns were not used in this experiment. These results were obtained with electrodes placed externally to the angiocatheter; however the electrodes may also be housed within the IV catheter. Placing the electrode inside the IV catheter will allow for improved detection of the electrical properties of the extra-vascular, sub-cutaneous tissues or of intra-vascular conditions.

Figure 5:
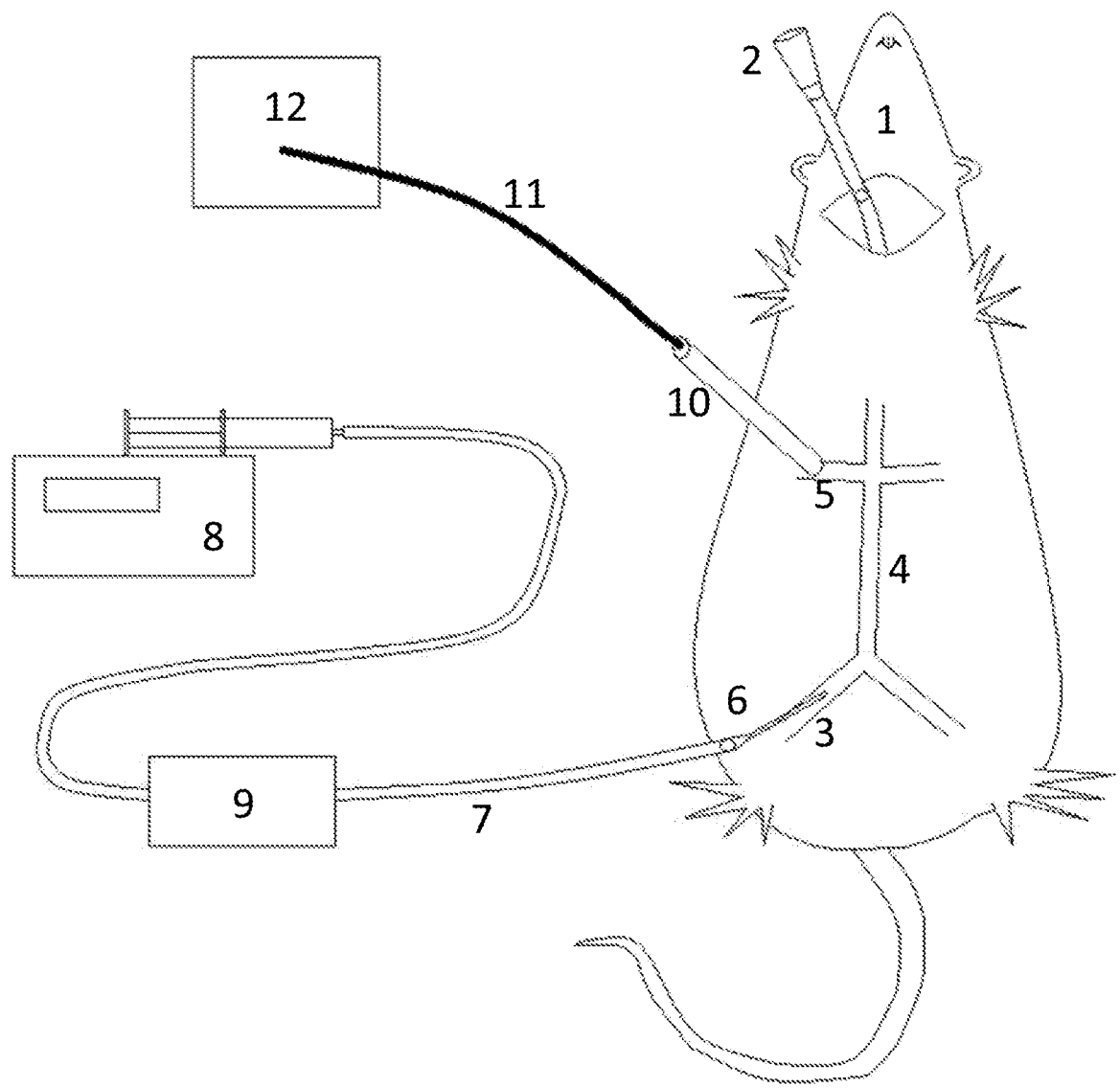
FIG. 5 shows an experimental set up for demonstration of the functionality of the intravenous signature impulse system.

FIG. 5 shows an experimental set up for demonstration of the functionality of the intravenous signature impulse system. An anesthetized Sprague-Dawley rat (1) maintained on a small animal ventilator (not shown) via a tracheostomy (2) underwent extended celiotomy with medialization of the intraperitoneal viscera to expose the right iliac vein (3), inferior vena cava (4), and right iliolumbar vein (5). The right iliac vein was cannulated with an 18 Ga angiocatheter (6) and 100 units/kg heparin was administered for systemic anticoagulation. The angiocatheter was connected via silicone intravenous tubing (7) to a syringe pump (8) (Pump 11 Elite, Harvard Apparatus, Holliston, Mass.) to maintain a constant intravenous infusion rate of normal saline. The inline impulse-generating apparatus (9) was applied to the intravenous tubing downstream of the syringe pump between the syringe pump and the experimental animal. A conventional Doppler probe (10) detected signal at the right iliolumbar vein (5) and was connected via connecting wires (11) to a signal processing unit (12) (Parks Medical Electronics, Inc, Beaverton, Oreg., Model 810-A) to generate an acoustic waveform.

Figure 6:
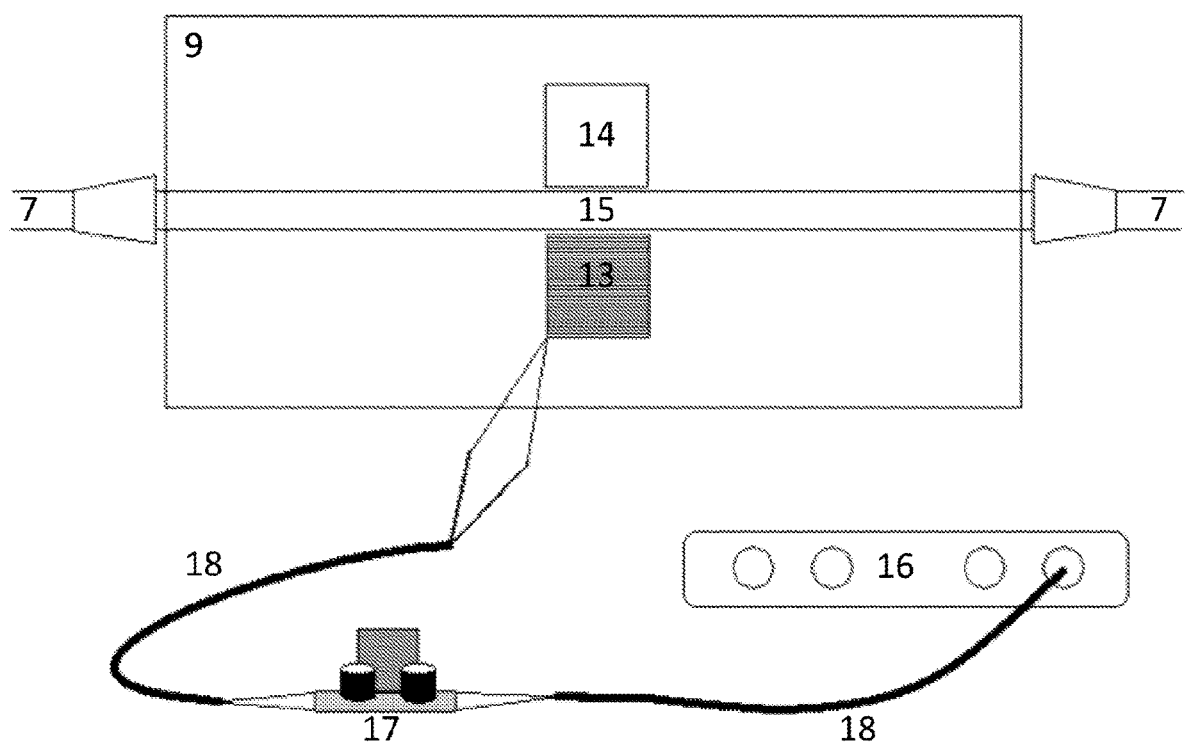
FIG. 6 depicts a schematic diagram of an in-line impulse-generating apparatus.

The inline impulse-generating apparatus (9) is detailed in FIG. 6. The intravenous tubing (7) was passed into the inline impulse-generating apparatus (9). In its simplest form, an inline impulse-generating apparatus surrounds a tube containing the liquid to be delivered to the patient. During use, the inline impulse-generating apparatus creates a fluid pulse by altering the diameter of the tube containing the liquid within the inline impulse generating apparatus. In one embodiment, the inline impulse-generating apparatus includes a magnetic coil (13) and permanent magnet (14) between which the silicone intravenous tubing (15) was passed; alternate attraction and repulsion of the magnetic coil with respect to the permanent magnet created compression followed by re-expansion of the flexible, silicone intravenous tubing resulting in a transmitted impulse through the fluid column within the tubing. The pattern of impulses delivered by the impulse-generating apparatus was determined by connection of the magnetic coil (13) to a signal generator (16) (Model 3204B, PicoScope, Cambridge, UK) amplified by a 7 watt amplifier (17) (model K4001, Velleman, Fort Worth, Tex.) via connecting wires (18). Regular vibratory impulse signals as well as more complex, extraphysiologic impulse patterns were possible with the arbitrary signal generator function of the oscilloscope (16).

Figure 7:
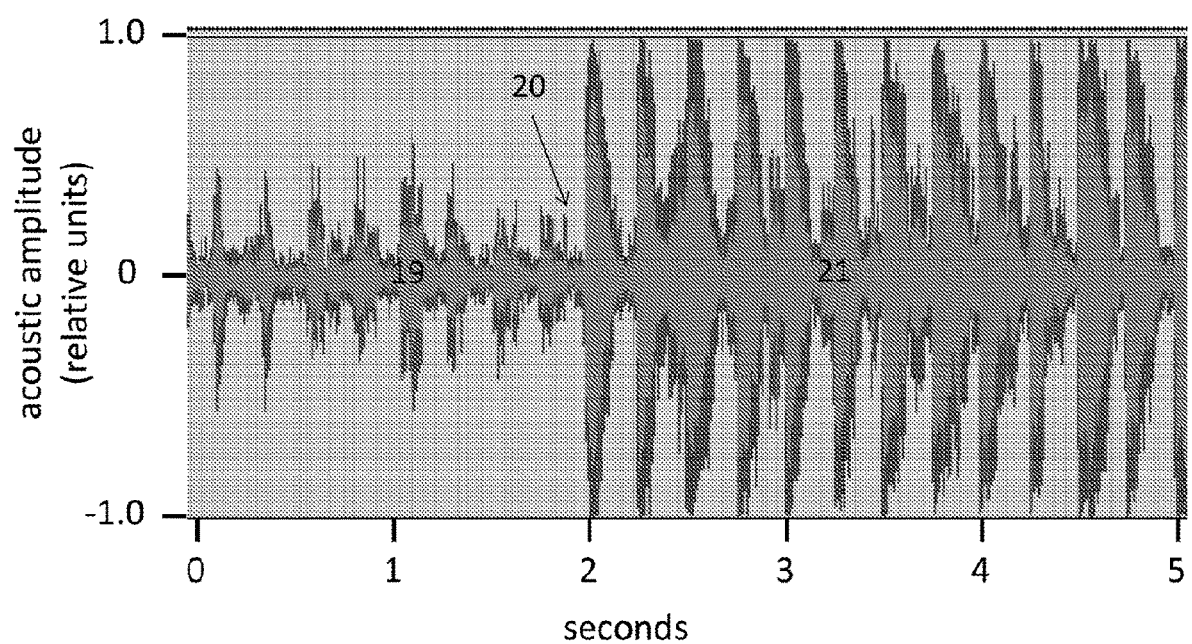
FIG. 7 shows an acoustic waveform generated in the experimental animal of FIG. 5 by the inline impulse generating apparatus.

FIG. 7 shows an acoustic waveform generated in the experimental animal of FIG. 5 by the inline impulse generating apparatus. Digital editing software (Audacity 2.0.1, http://audacity.sourceforge.net/) was used to create an acoustic waveform display with maximum recording peaks of −6 dB (y-axis linear acoustic values (+/−1.0 relative units), x-axis time (seconds)). The intravenous infusion rate was set at 10 ml/hr by the syringe pump (FIG. 5, 8) and an acoustic signal was generated by the Doppler flow meter (FIG. 5, 10-12). First, a Doppler signal was obtained from the right iliolumbar vein prior to activation of the impulse-generating apparatus (19). Some low background signal due to artifactual detection of adjacent arterial pulsatile signal was present (19) but largely a lack of distinctive signal was present in the iliolumbar vein prior to activation of the impulse-generating apparatus. Next, the impulse-generating apparatus was activated (20) by turning on the signal generator (FIG. 6, 16) with signal pattern of a 4 Hz square wave. Under these conditions, a 4 Hz signal was generated in the venous system resulting in a clearly detectable and distinguishable Doppler impulse pattern (21).

Figure 8:
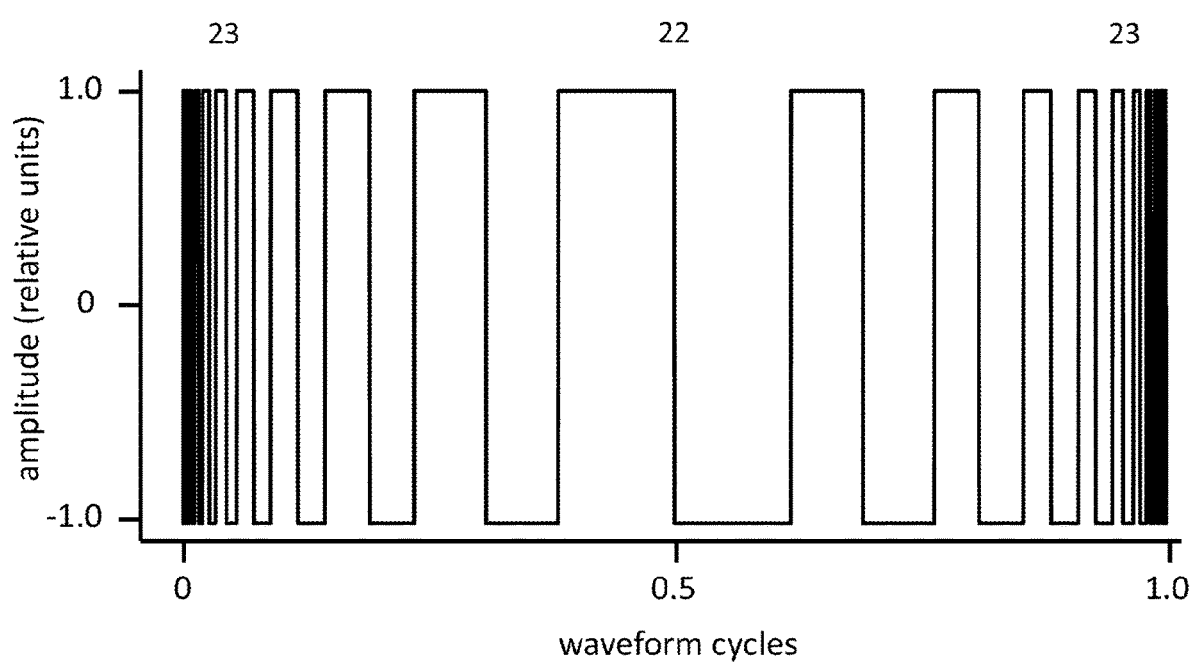
FIG. 8 illustrates a waveform that includes a frequency-modulated waveform with frequency ratio variation based on a defined number series.

Other waveforms may be used by using the arbitrary signal generator function of the function generator (FIG. 6, 16). FIG. 8 illustrates one such possible complex waveform consisting of a frequency-modulated waveform with frequency ratio variation based on a defined number series (0, 1, 1, 2, 3, 5, 8 . . . ). This pattern was defined by areas of relatively low frequency square waves (22) interspersed with areas of higher frequency square waves (23) to produce an impulse pattern within the venous system which bore no resemblance to and as a result could be readily distinguished from background physiologic pulses or cadences.

Figure 9:
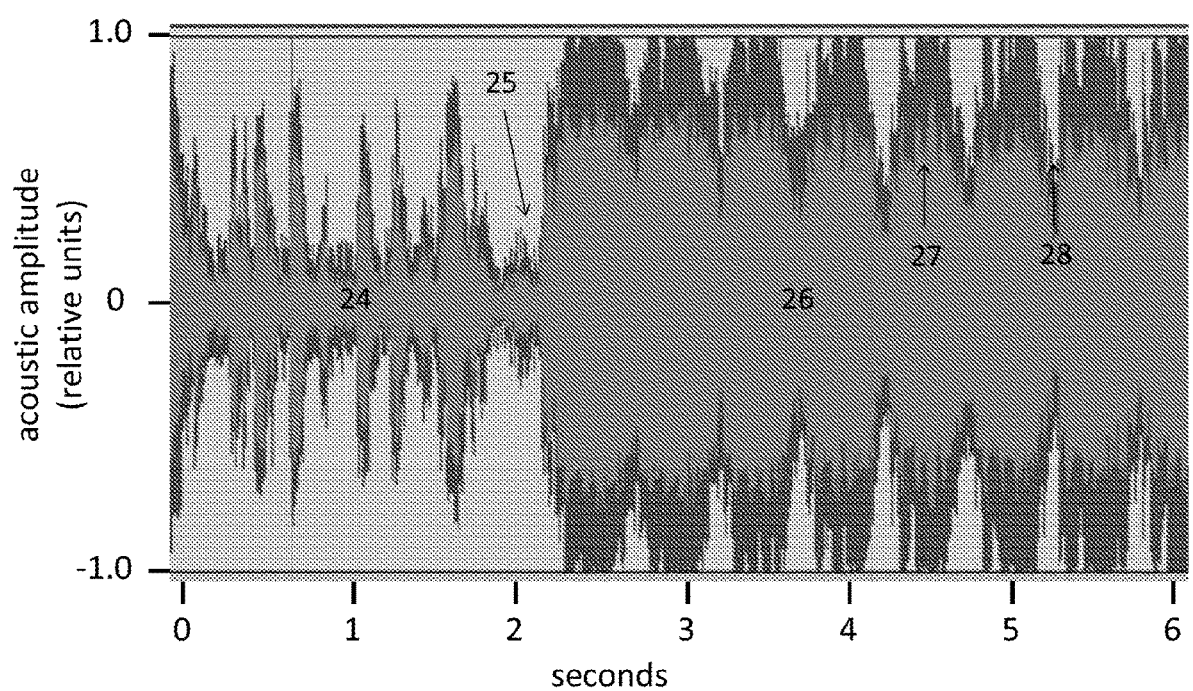
FIG. 9 shows an acoustic waveform generated in the experimental animal of FIG. 5 as generated by the impulse pattern designated in FIG. 8.

FIG. 9 shows an acoustic waveform generated in the experimental animal of FIG. 5 as generated by the impulse pattern designated in FIG. 8. Digital editing software (Audacity 2.0.1) was used to create an acoustic waveform display with maximum recording peaks of −6 dB (y-axis linear acoustic values (+/−1.0 relative units), x-axis time (seconds)). The intravenous infusion rate was set at 10 ml/hr by the syringe pump (FIG. 5, 8) and an acoustic signal was generated by the Doppler flow meter (FIG. 5, 10-12). First, a Doppler signal was obtained from the right iliolumbar vein prior to activation of the impulse-generating apparatus (24). Some low background signal due to artifactual detection of adjacent arterial pulsatile signal was present (24) but largely a lack of distinctive signal was present in the iliolumbar vein prior to activation of the impulse-generating apparatus. Next, the impulse-generating apparatus (FIG. 6, 16) was activated (25) following a signal pattern of the frequency modulated pattern illustrated in FIG. 8 at a frequency of 2 Hz. Under these conditions, a signal was generated in the venous system resulting in a clearly detectable and distinguishable Doppler impulse pattern with areas of high signal frequency (27) and lower frequency (28) paralleling the high and low frequency regions of the waveform illustrated in FIG. 8.

Figure 10:
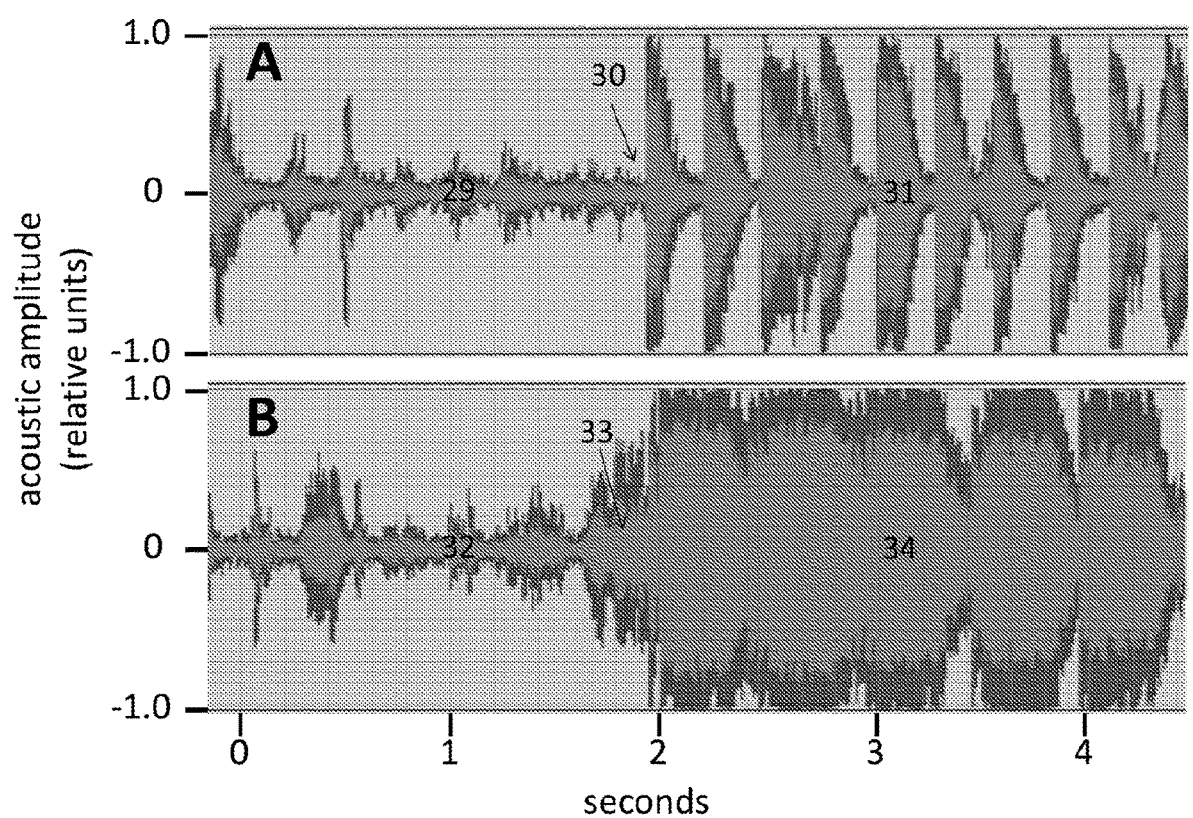
FIG. 10A depicts the acoustic signal detected from the right iliolumbar vein prior to, and during, activation of the impulse generating apparatus, the signal generated by a 4 Hz square wave.
FIG. 10B depicts the acoustic signal prior to, and during, activation of the impulse generating apparatus, the signal generated by the impulse pattern designated in FIG. 8 at a frequency of 2 Hz.
Figure 11:
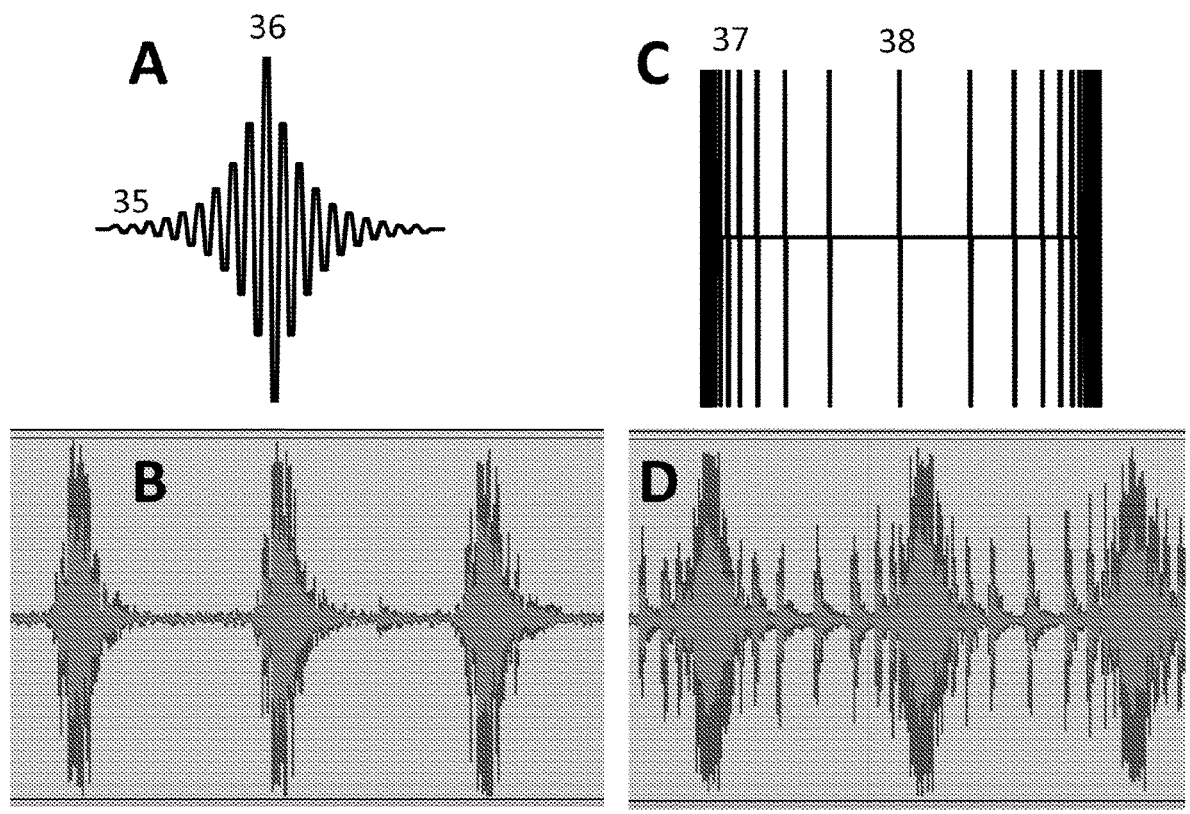
FIG. 11A illustrates an amplitude-modulated waveform with amplitude ratio variation based on a defined number series.
FIG. 11B illustrates the detected impulse pattern within the venous system of the waveform of FIG. 11A.
FIG. 11C illustrates a frequency-modulated waveform with frequency ratio variation based on a defined number series.
FIG. 11D illustrates the detected impulse pattern within the venous system of the waveform of FIG. 11C.
Figure 12:
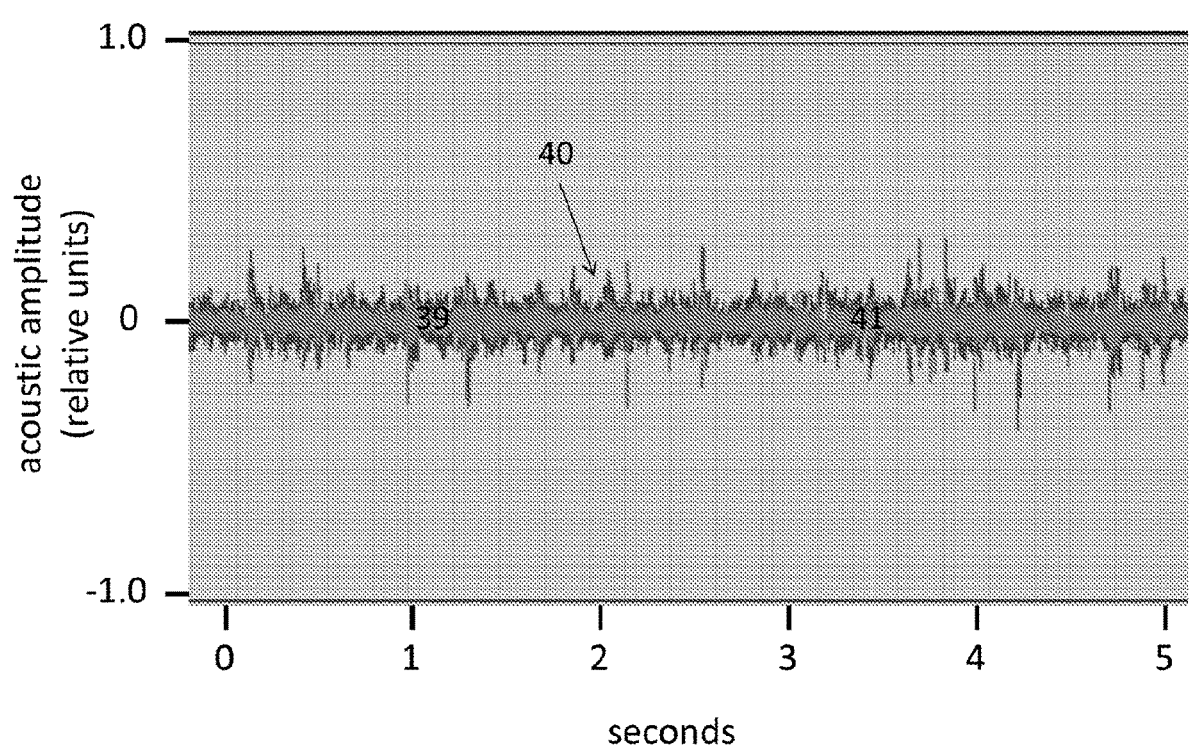
FIG. 12 depicts a signature impulse pattern in the intravenous system detected via an intravenous catheter using the impulse generating apparatus.

FIG. 10 demonstrates that no forward intravenous flow was required for the inline impulse generating apparatus to establish an acoustic signature in the venous system. The same experimental animal illustrated in FIG. 5 was employed for this experiment. The positioning of the components of the experimental set up remained unchanged however instead of the syringe pump set to deliver an intravenous fluid rate of 10 ml/hr, the flow rate was set at 0 ml/hr; this simulates an intravenous catheter at heparin lock or saline lock, i.e, when an intravenous catheter remains in place in a patient but is not being actively used to conduct intravenous fluids or medications. FIGS. 10A and 10B depict acoustic waveforms. FIG. 10A depicts the acoustic signal detected from the right iliolumbar vein prior to activation of the impulse generating apparatus (29) followed by activation of the impulse generating apparatus (30) and the signal generated by a 4 Hz square wave (31). FIG. 10B depicts the acoustic signal prior to activation of the impulse generating apparatus (32), followed by activation of the impulse generating apparatus (33) and the signal generated by the impulse pattern designated in FIG. 8 at a frequency of 2 Hz (34). The fact that no net forward flow of intravenous fluid was required to establish vibratory impulses within the fluid column of the intravenous system represents an important clinical feature of the impulse-generating system. It shows that even an intravenous catheter that is idle (i.e. not actively being used to deliver medications or fluids) can be used to carry a signal which confirms its patency.

Other complex waveforms were tested. FIG. 11A illustrates an amplitude-modulated waveform with amplitude ratio variation based on a defined number series (0, 1, 1, 2, 3, 5, 8 . . . ). This pattern was marked by areas of relatively low amplitude square waves (35) interspersed with areas of higher amplitude square waves (36) to produce an impulse pattern within the venous system (FIG. 11B) which bore no resemblance to and as a result could be readily distinguished from background physiologic pulses or cadences. FIG. 11C illustrates a frequency-modulated waveform with frequency ratio variation based on a defined number series (0, 1, 1, 2, 3, 5, 8 . . . ) but shortened duration of the constituent square-waves marked by regions of higher frequency (37) and lower frequency (38) short square wave pulses that produced an impulse pattern within the venous system (FIG. 11D) which bore no resemblance to and as a result could be readily distinguished from background physiologic pulses or cadences FIG. 12 demonstrates that the ability to impart a signature impulse pattern in the intravenous system via an intravenous catheter using the impulse generating apparatus was predicated on a continuous column of fluid within the intravenous tubing, catheter, and venous system. For this experiment, the same experimental animal as illustrated in FIG. 5 was used without alteration of the experimental set up. The intravenous catheter (FIG. 5, 6) was temporarily disconnected from the intravenous tubing (FIGS. 5, 7) and 2 cc of fibrin sealant (Evicel, Ethicon, Somerville, N.J.) was injected into the intravenous catheter to create coagulation/thrombosis within the catheter and venous system to duplicate the conditions encountered during intravenous catheter thrombosis. The syringe pump (FIG. 5, 8) was set to deliver an intravenous fluid rate of 10 ml/hr. Doppler readings were obtained from the right iliolumbar artery. Readings were obtained prior to activation of the impulse generating apparatus (39), then the impulse generating apparatus signal was turned on (40) and readings were obtained with the signal activated (41). No signal change was detected between signal off (39) and signal on (41) of the impulse generating apparatus. This demonstrates that the signal delivered into the venous system by the impulse generating apparatus and detected by Doppler in FIGS. 7, 9, and 10 was not conducted by the walls of the intravenous tubing or by the walls of the vein but by an uninterrupted column of fluid within these conduits; interruption of this column of fluid abrogated signal transmission. This also demonstrates an important clinical characteristic of this system of detection of intravenous extravasation. The first event that occurs in intravenous infiltration is coagulation/thrombosis of the vein harboring an intravenous catheter; extravasation follows as a later step as coagulant blocks delivery of fluids and/or medications into the intravascular space and they are diverted into the subcutaneous tissues. Ideally, a system of identifying/preventing intravenous infiltration would focus on the early identification of coagulation/thrombosis so that subsequent extravasation of fluids/medications into the subcutaneous tissues could be minimized. This system appears effective at identifying coagulation/thrombosis and as such appears to be an early detector of the cascade of intravenous extravasation.

While the choice of an oscilloscope coupled to a magnetic coil to comprise the impulse generating apparatus allowed for mathematically defined patterns of mechanical force to be applied to the intravenous tubing as a means of establishing signature impulse flow patterns in the intravascular fluids, many other potential mechanisms of delivering mechanical force in precise sequences to the intravenous tubing are possible and may be more practical for clinical use in patients. Rotating gears with gear teeth configured to strike the IV tubing at defined time intervals could produce signature impulse patterns. Alternatively, rotating cams producing precisely defined rise, return, and dwell intervals in a follower that strikes the IV tubing could also be designed to produce signature impulse patterns. Or pumps could be designed with special components to deliver signature impulse patterns such as: centrifugal pumps, rotary or linear peristaltic pumps, piston pumps, or multiplex pumps, or other types of fluid pumps. Diaphragms or appendages could also be constructed into the intravenous tubing to facilitate the transfer of mechanical energy from the impulse generating apparatus to the intravascular fluids.

The intravenous impulse generation system may also act to prevent intravenous catheter coagulation/thrombosis. Virchow's triad of venous stasis, venous trauma, and a procoagulant state identifies increased risk of venous thrombosis in patients. Typical intravenous fluid or medication flows are very low and flow is zero when an intravenous catheter is idle (i.e. to saline or heparin lock). These factors promote venous stasis. By applying back-and-forth flow to an otherwise static intravenous system, impulse generation has the potential to reduce venous stasis thereby reducing the risk of thrombosis. Additionally, the tip of an intravenous catheter may represent a site of trauma to a peripheral vein by contact with and irritation of the endovascular surface of the vein. Impulse generation may reduce the likelihood of trauma at the tip of the intravenous catheter by effectively creating a cushion of back-and-forth fluid flow between the tip of the intravenous catheter and the wall of the vein, thereby reducing the risk of thrombosis. Finally, impulse generation in the venous system may have a similar effect to sequential compression devices in the prevention of venous thrombosis. Sequential compression devices have been shown to decrease the likelihood of deep venous thrombosis in part through promoting anti-coagulant blood factors; intravenous impulse generation may have a similar effect.

The signal generated by the inline-impulse generating apparatus could also be detected by an intravenous catheter configured to house electrodes able to detect changes in electrical resistance. FIG. 13A shows an 18-gauge angiocatheter (42) to which fine gauge insulated copper wires (43) were affixed on the exterior of the angiocatheter using parafilm (44). At the end of the wires near the outflow end of the angiocatheter, the insulation layer around the wires was removed to allow the bare metal of the wires to be exposed (45). The parafilm covering (44) extended slightly beyond the outflow end of the angiocatheter (46) so as to insulate the wires electrically from the wall of the vein but to allow contact between the bare metal of the wires inside the parafilm sheath with the fluid passing out of the angiocatheter and into the vein. FIG. 13B shows a cross-section of the relationship of the angiocatheter (42), the wires (43) and the parafilm covering (44).

Figure 13:
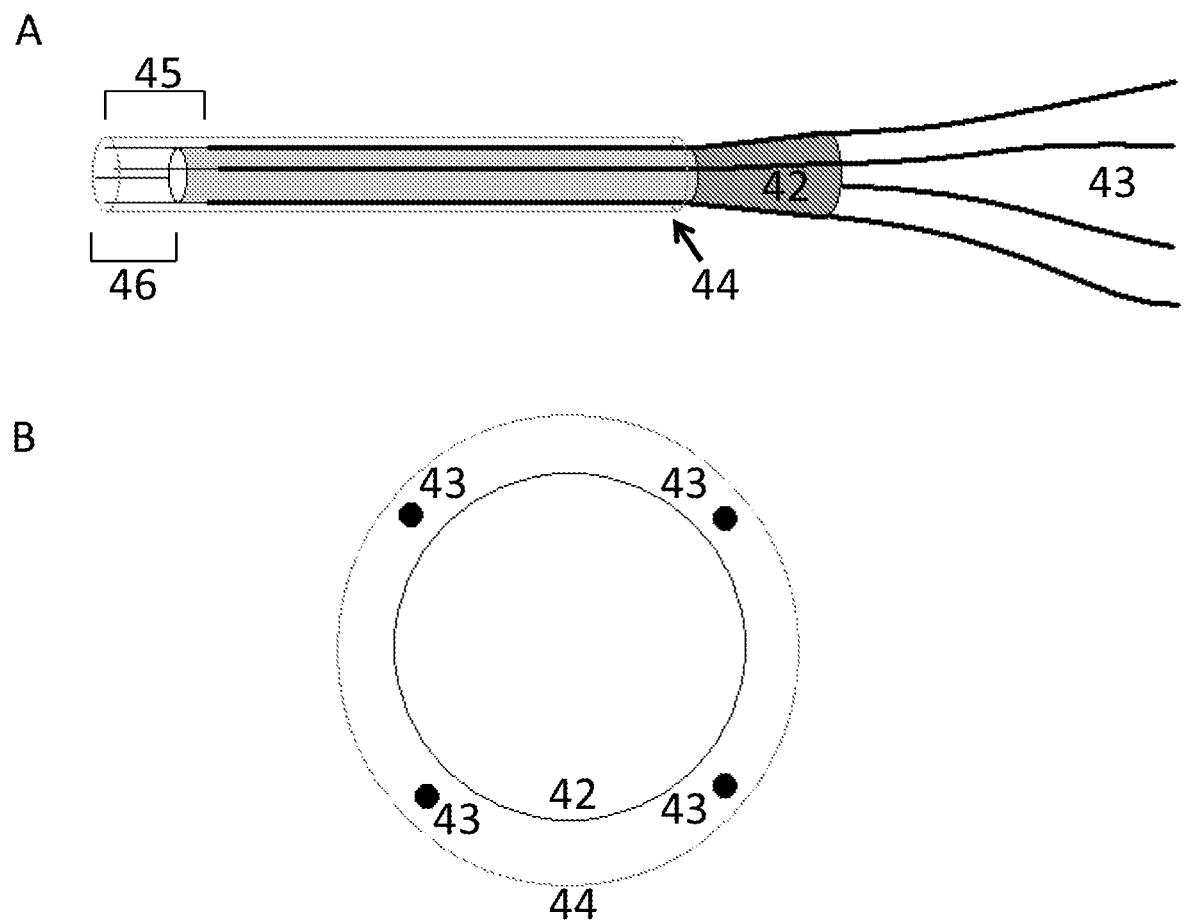
FIG. 13A depicts a side view of an angiocatheter to which insulated wires are affixed on the exterior of the angiocatheter.
FIG. 13B depicts an end vies of the angiocatheter of FIG. 13A.
Figure 14:
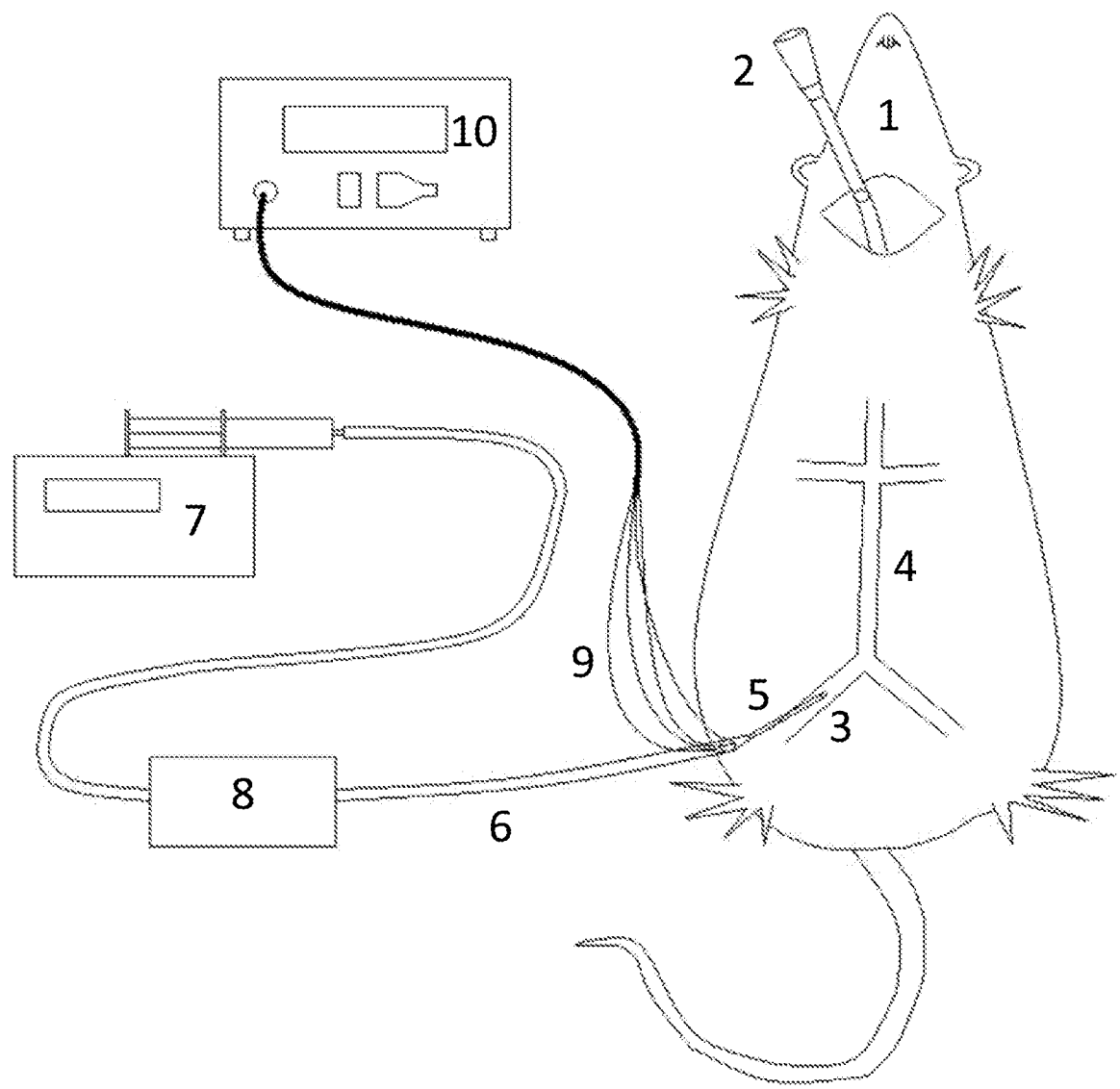
FIG. 14 shows an experimental set up for demonstrating the functionality of the intravenous signature impulse system based on electrical resistance changes induced by the inline impulse generating apparatus as detected by an angiocatheter having electrodes able to detect changes in electrical resistance.

FIG. 14 shows an experimental set up for demonstrating the functionality of the intravenous signature impulse system based on electrical resistance changes induced by the inline impulse generating apparatus as detected by an angiocatheter configured to house electrodes able to detect changes in electrical resistance. An anesthetized Sprague-Dawley rat (1) maintained on a small animal ventilator (not shown) via a tracheostomy (2) underwent extended celiotomy with medialization of the intraperitoneal viscera to expose the right iliac vein (3) and inferior vena cava (4). The right iliac vein (or alternatively the inferior vena cava) was cannulated with the electrode-containing 18 Ga angiocatheter illustrated in FIG. 13 (5) and 100 units/kg heparin was administered for systemic anticoagulation. The angiocatheter was connected via silicone intravenous tubing (6) to a syringe pump (7) (Pump 11 Elite, Harvard Apparatus, Holliston, Mass.) to maintain a constant intravenous infusion rate of normal saline. The inline impulse-generating apparatus (8, detailed in FIG. 6) was applied to the intravenous tubing downstream of the syringe pump between the syringe pump and the experimental animal. Connecting wires (9, corresponds to FIG. 13, 43) emanating from the electrode-containing angiocatheter were connected to an electrical resistance measuring unit (10) (Quantum-II Desktop bioimpedance device, RJL Systems, Clinton Township, Mich.). Dynamic resistance was measured to the nearest 0.1 ohms.

Figure 15:
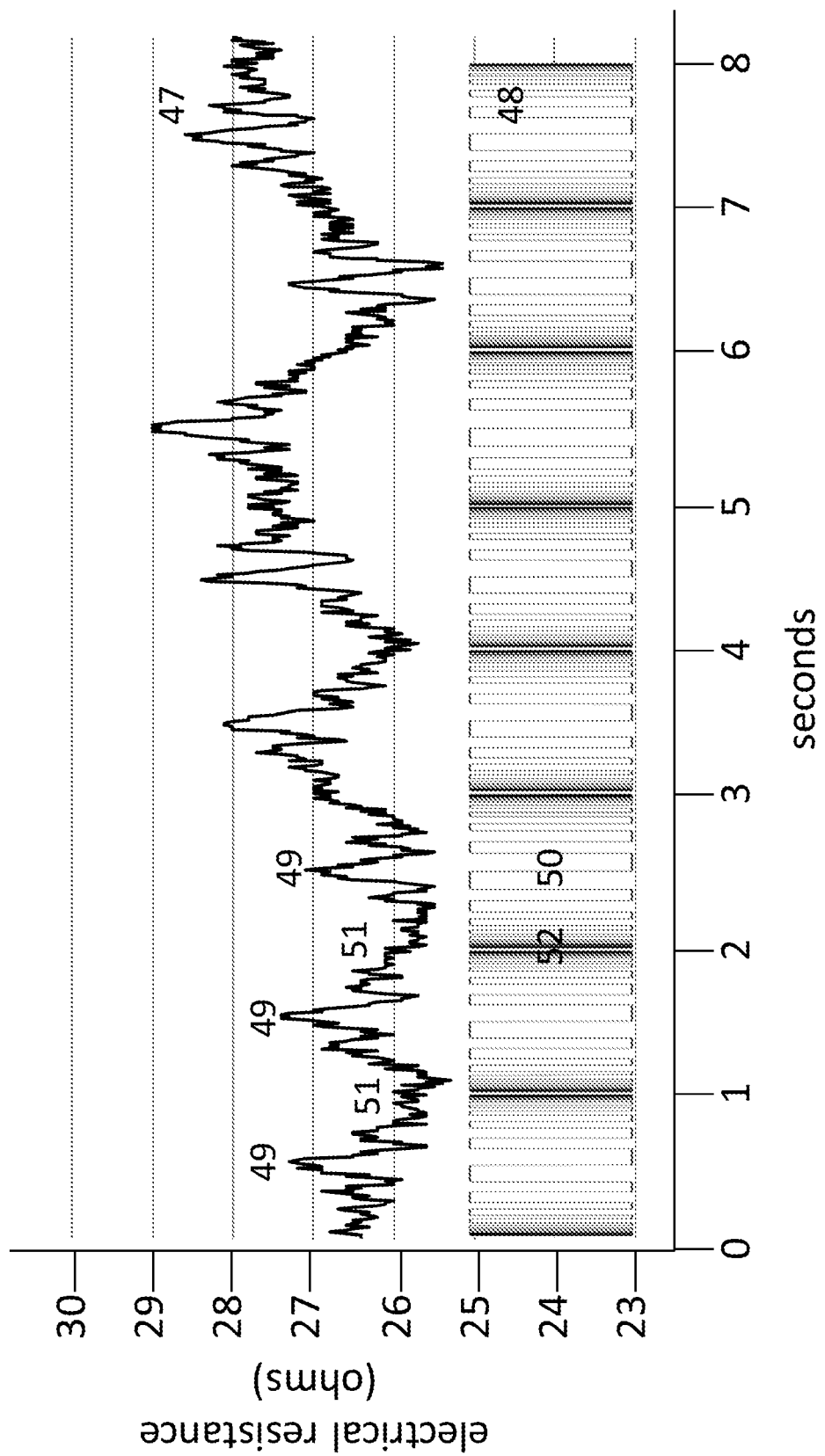
FIG. 15 depicts the electrical resistance tracing as sensed by the bare-metal portion of the angiocatheter-embedded electrodes (FIG. 13) and measured by the resistance measuring device (FIG. 14) using the signature impulse pattern illustrated in FIG. 8.

FIG. 15 shows the electrical resistance tracing (47) as sensed by the bare-metal portion of the angiocatheter-embedded electrodes (FIG. 13, 45) and measured by the resistance measuring device (FIG. 14, 10) using the signature impulse pattern illustrated in FIG. 8 consisting of a frequency-modulated waveform with frequency ratio variation based on a defined number series (0, 1, 1, 2, 3, 5, 8 . . . ) repeated at a rate of one full waveform per second (1 Hz). An overlay of the frequency modulated waveform (48) (from FIG. 8) used to program the signal generator component of the inline impulse generating apparatus (FIG. 14, 8, detailed in FIG. 6) shows how the detected electrical resistance tracing (47) corresponded to the programmed waveform. The electrical resistance tracing (47) was marked by high peak resistance changes occurring at 1 Hz intervals (49) which corresponded to the lower frequency portion (50) of the frequency modulated waveform. Flanking the high peak resistance changes (49) were regions of diminishing magnitude resistance change peaks (51) corresponding to areas of increasingly higher frequency (52) of the frequency modulated waveform. The lower frequency portions of the frequency modulated signal (50) allowed more time for displacement of the magnetic coil portion of the in-line impulse-generating apparatus (FIG. 6, 13) from the permanent magnet (FIG. 6, 14) resulting in stronger mechanical force applied to the intravenous tubing and a higher peak displacement of the intravenous contents ultimately producing a high peaked resistance change (49) as sensed by the angiocatheter-housed electrodes (FIG. 13, 45).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of providing intravenous fluids to a subject comprising:
   providing a system for monitoring a venous fluid flow in the subject, the system comprising:
      a pump system that, during use, delivers a fluid to a blood vessel of the subject via an intravenous catheter or cannula, wherein the pump system comprises a pump and an inline impulse generating apparatus, wherein the inline impulse generating apparatus creates a pressure pattern in the fluid; and
      a probe coupled to the blood vessel, the probe being capable of detecting vibratory impulses corresponding to pressure changes of the fluid in the blood vessel;
   coupling an intravenous fluid source to the pump system;
   inserting the intravenous catheter or cannula into the blood vessel of the subject;
   positioning the probe at a position that is upstream, with respect to a flow of blood through the blood vessel, from a location of the intravenous catheter or cannula;
   sending intravenous fluid from the intravenous fluid source to the subject through the intravenous catheter or cannula;
   setting the pump to deliver a flow rate at zero;
   creating a predetermined pressure pattern in the intravenous fluid while the deliver flow rate is at zero, wherein a net forward flow rate of the intravenous fluid, when the predetermined pressure pattern is created, is zero; and
   monitoring vibratory impulses corresponding to pressure changes of the fluid in the blood vessel using the probe while there is no flow from the intravenous fluid source.

2. The method of claim 1, wherein the intravenous fluid comprises blood or plasma.

3. The method of claim 1, wherein the intravenous fluid comprises saline.

4. The method of claim 1, wherein the intravenous fluid comprises medicine.

5. The system of claim 1, wherein the pressure pattern comprises a pattern of pulses.

6. The system of claim 5, wherein the pattern of pulses comprises amplitude modulated pulses.

7. The system of claim 5, wherein the pattern of pulses comprises frequency modulated pulses.

8. The method of claim 1, wherein the pressure pattern comprises a pattern of pulses.

9. The method of claim 8, wherein the pattern of pulses comprises amplitude modulated pulses.

10. The method of claim 8, wherein the pattern of pulses comprises frequency modulated pulses.

* * * * *